United States Patent
Jackson et al.

(10) Patent No.: US 6,229,057 B1
(45) Date of Patent: *May 8, 2001

(54) CHLORINATION PROCESS

(75) Inventors: Alan Raymond Jackson, Liverpool; Sean James Doyle; Keith Moorhouse, both of Huddersfield; Thomas Gray, Wakefield, all of (GB)

(73) Assignee: Zeneca Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/571,886

(22) PCT Filed: Jul. 25, 1994

(86) PCT No.: PCT/GB94/01591

§ 371 Date: Jan. 11, 1996

§ 102(e) Date: Jan. 11, 1996

(87) PCT Pub. No.: WO95/03264

PCT Pub. Date: Feb. 2, 1995

(30) Foreign Application Priority Data

Jul. 26, 1993 (GB) .................................................. 9315450

(51) Int. Cl.$^7$ ......................... C07C 17/013; C07C 19/08; C07C 19/043

(52) U.S. Cl. ............................................ 570/123; 570/124

(58) Field of Search ............................................. 570/123

(56) References Cited

U.S. PATENT DOCUMENTS

| | | | |
|---|---|---|---|
| 2,469,290 | | 5/1949 | Calfee et al. .................... 204/157.95 |
| 2,724,718 | * | 11/1955 | Stiles et al. ........................ 568/894 |
| 3,047,642 | * | 7/1962 | Wolf ..................................... 570/123 |
| 4,060,469 | | 11/1977 | Sweeney et al. ............... 204/158.11 |
| 5,120,883 | * | 6/1992 | Rao et al. ............................ 570/123 |
| 5,254,771 | * | 10/1993 | Cremer et al. ....................... 570/123 |
| 5,315,044 | | 5/1994 | Furutaka et al. .................... 570/123 |
| 5,414,164 | * | 5/1995 | Brown et al. ........................ 570/123 |

FOREIGN PATENT DOCUMENTS

| | | |
|---|---|---|
| 407990 | 1/1991 | (EP) . |
| 904831 | 8/1962 | (GB) . |
| 2269381 | 2/1994 | (GB) . |
| 90/08752 * | 8/1990 | (WO) . |

* cited by examiner

*Primary Examiner*—Alan L. Rotman

(57) ABSTRACT

There is provided a process for the preparation of 1,1,1-trichlorotrifluororethane in which 1,1-dichloro-2,2,2-trifluoroethane is subjected to chlorination by bringing the 1,1-dichloro-2,2,2-trifluoroethane into contact with chlorine within a reaction vessel characterised in that the process is conducted in the liquid phasein the presence of a chemical free radical initiator under a pressure of from 1 to 20 bar and at a temperature within the range 50 to 120° C., and the product is separated from the reaction mixture by fractional distillation. The product is useful in the manufacture of insecticides.

12 Claims, No Drawings

CHLORINATION PROCESS

This application is a 371 of PCT/GB 94/01591 filed Jul. 25, 1994.

This invention relates to a chlorination process for the preparation of 1,1,1-trichlorotrifluoroethane.

1,1,1-Trichlorotrifluoroethane is a valuable chemical intermediate which is used, inter alia, in the preparation of precursors of pyrethroid insecticides, such as cyhalothrin and tefluthrin. Hitherto it has been obtained by various processes including by rearrangement of the isomeric product 1,1,2-trichlorotrifluoroethane in the presence of aluminium halides, and by gas-phase photochemically-initiated chlorination of non-perhalogenated precursors such as 1,1,1-trifluoroethane. However the use of these processes is considered unsatisfactory because of low conversion rates, difficulty in separating the product from the starting material, and/or the formation of undesirable by-products.

It has now been found that by careful selection of the conditions it is possible to obtain 1,1,1-trichlorotrifluoroethane by chlorination of 1,1-dichloro-2,2,2-trifluoroethane, and the process is capable of providing a high degree of conversion with high specificity and easy separation of the desired product. Furthermore it is possible to adapt the process to operate not only on a batch by batch basis but also in a semi-continuous or continuous manner suitable for large scale manufacture of 1,1,1-trichlorotrifluoroethane.

Accordingly the present invention provides a process for the preparation of 1,1,1-trichlorotrifluoroethane in which 1,1-dichloro-2,2,2-trifluoroethane is subjected to chlorination by bringing the 1,1-dichloro-2,2,2-trifluoroethane into contact with chlorine within a reaction vessel characterised in that the process is conducted in the liquid phase in the presence of a chemical free radical initiator under a pressure of from 1 to 20 bar and at a temperature within the range 50 to 120° C., and the product is separated from the reaction mixture by fractional distillation.

In the case of continuous or semi-continuous operation the reactants are continuously fed into the reaction vessel at a rate consistent with the steady state production of 1,1,1-trichlorotrifluoroethane and within a preferred molar ratio of chlorine to 1,1-dichloro-2,2,2-trifluoroethane within the range 1.0 to 2.5. At the steady state the molar ratio of chlorine to total chlorinatable hydrogen atoms is also preferably within the range 0.5 to 1.0.

The process is conducted within a closed system with arrangements to admit the reactants and remove the product. All the components may be admitted at one location, typically at a low point on the reactor so that the chlorine rises through the liquid. In an alternative arrangement the chlorine can be admitted at a low point whilst the other components are admitted at a higher point so that a counter current is created enabling more efficient mixing. Within the reaction vessel itself the conditions of the process may be controlled by regulation of the rate of addition of the reactants, the reaction temperature and the pressure under which the reaction is conducted. In particular the rates of the potentially competing reactions may be influenced by the choice of temperature and pressure. Pressure is partially dependent on the relative vapour pressure contributions of all the components in the gaseous phase which is in equilibrium with the liquid phase in which the reaction occurs, and may be augmented by introducing pressurised inert gas, for example nitrogen. For optimum conversion the pressure is preferably maintained within the range 5 to 15 bar and more preferably within the range 7 to 13 bar.

The temperature at which the process is conducted is also an important determinant of optimum conversion and is preferably within the range 80 to 110° C.

The process is conducted in the presence of a chemical free-radical initiator intended to catalyse the production of chlorine radicals to promote the chlorination reaction. Suitable free-radical initiators include for example aroyl peroxides such as dibenzoyl peroxide, and azo compounds such as azobisisobutyronitrile, which is particularly preferred. It is preferred that me initiator be present at a constant amount during the process and therfore where continuous operation is used the initiator may be fed continuously at a constant rate in proportion to the continuous addition of the reactants. It is also prefered that the initiator be present in a dissolved form to maximise its effect and to avoid the complications arising from a the presence of a solid phase in the reaction vessel. This is best achieved by dissolving the initiator in a suitable solvent which is either non-reactive or is itself consumed in the process to produce the desired product. Certain non-perhalogenated precursors of 1,1,1-trichlorotrifluoroethane are particularly suitable including 1-chloro-2,2,2-trifluoroethane and 1,1-dichloro-2,2,2-trifluoroethane itself.

A particularly preferred combination of conditions for conducting the reaction in a continuous manner comprises carrying out the process at a pressure within the range 7 to 13 bar and a temperature within the range 80 to 120° C. in the presence of azobisisobutyronitrile whilst continuously feeding the reactants at a molar ratio of chlorine to 1,1-dichloro-2,2,2-trifluoroethane within the range 1.2 to 1.4.

Preferably the azobisisobutyronitrile is present at a concentration within the range 1000 to 5000 ppm.

The product, which is present as a substantial component of the reaction mixture is separated from the other components by a process of fractional distillation. The other components of the reaction mixture are unreacted chlorine and unreacted 2,2-dichloro-3,3,3-trifluoroethane. After separation these other components can be recycled into the reaction vessel in order to maximise the conversion to the desired product. Fractional distillation provides a simple method of separating the components of the reaction mixture because of the differences in boiling points which are 26° C. for 1,1-dichloro-2,2,2-trifluoroethane and 46° C. for 1,1,1-trichlorotrifluoroethane.

Typically the process is operated by passing a premixed stream of the reactants into the reactor, which may be for example a bubble column chlorinator, into which a solution of the initiator is also being introduced, the rates of addition being controlled so as to allow the contents of the reactor to reach a steady state composition in which product predominates, and to continuously remove the contents, as the product stream, at a rate consistent with the rate of addition of the reactants. Thereafter the product stream is passed into a still and fractionated to obtain the 1,1,1-trichlorotrifluoroethane free from the other components of the stream which are recycled back into the reactant stream.

In the process in which the reactant stream includes recycled components the steady state composition (excluding chlorine) may contain from about 40% to 85% by weight of the desired 1,1,1-trichlorotrifluoroethane and less than about 60% by weight of 1,1-dichloro-2,2,2-trifluoroethane. It is an advantage of the process that there is little or no formation of unwanted dimeric or polymeric by-products, and consequently a very high yield with respect to the desired product when recycling is taken into account.

The invention process is illustrated by the following Examples in which the process was conducted in a bubble column chlorinator with a capacity of 950 ml, the center section of which was fitted with a jacket heater and the upper portion, above the liquid level when filled, surrounded by a cooling jacket cooled by circulating butanol at −25° C. The column was connected to a supply of nitrogen under pressure. In Examples 1 and 2 the components were fed into the bottom of the column at predetermined rates and ratios and the reaction allowed to proceed until a steady state, as shown by sampling the reaction mixture until an unchanging composition (as determined by gas chromatography) was reached. In Examples 3 to 7 the chlorine was fed into the bottom of the column and the other components fed in at the top so as to produce a counter current.

In the examples the reactants and products are designated as follows:

Chlorine—$Cl_2$;

1,1-dichloro-2,2,2-trifluoroethane—DCTFE;

1,1,1-trichlorotrifluoroethane—TCTFE.

azobisisobutyronitrile—AIBN

EXAMPLE 1

The reactor was filled to the liquid level with DCTFE and pressured up to 120 psig with nitrogen. The contents were heated to 100° C. and the reactants continuously fed in at the following rates:

DCTFE 2.18 g/min

AIBN 4.36 mg/min (added as 0.2% solution in TCTFE)

$Cl_2$ 800 sccm

During the addition the temperature was maintained within the range 90 to 103° C. and the pressure was within the range 120 to 127 psig. A steady state composition (excluding chlorine) was achieved after about 165 minutes, as follows:

TCTFE 43.91%

DCTFE 56.01%

EXAMPLE 2

The process was conducted in a similar manner to Example 1 except the reactor was filled with a 1:1 mixture by weight of DCTFE and and the feed rates were as follows:

| | |
|---|---|
| DCTFE | 1.05 g/min |
| TCTFE | 1.05 g/min |
| AIBN | 8.37 mg/min |
| $Cl_2$ | 400 sccm |

A steady state composition (excluding chlorine) was obtained after 220 minutes, as follows:

| | |
|---|---|
| TCTFE | 78.89% |
| DCTFE | 20.26% |

EXAMPLES 3 TO 7

In these Examples the column was operated in a counter-current on by feeding the chlorine in at the bottom of the column and the components were fed in at the top. The conditions of temperatures pressure and the feed rates of the components is given in Table I and the steady state composition of the mixture produced and the off rate of the DCTFE and TCTFE given in Table II. Feed rates and off rates are expressed in gram moles per hour.

TABLE I

| Example No | Temp (° C.) | Pressure (barg) | Feed Rates DCTFE | Feed Rates TCTFE | Feed Rates $Cl_2$ | AIBN Concentration (ppm) |
|---|---|---|---|---|---|---|
| 3 | 102 | 8.45 | 0.380 | 0.311 | 0.371 | 2000 |
| 4 | 98 | 8.45 | 0.427 | 0.310 | 0.245 | 4000 |
| 5 | 100 | 8.50 | 0.399 | 0.326 | 0.204 | 2000 |
| 6 | 100 | 8.50 | 0.347 | 0.283 | 0.204 | 2000 |
| 7 | 101 | 8.50 | 0.343 | 0.280 | 0.390 | 4000 |

TABLE II

| Example No | Steady state composition (%) DCTFE | Steady state composition (%) TCTFE | Take-off rate DCTFE | Take-off rate TCTFE |
|---|---|---|---|---|
| 3 | 28.407 | 71.045 | 0.23 | 0.47 |
| 4 | 20.146 | 79.002 | 0.187 | 0.593 |
| 5 | 22.693 | 76.443 | 0.190 | 0.524 |
| 6 | 21.560 | 75.591 | 0.163 | 0.467 |
| 7 | 21.765 | 77.940 | 0.164 | 0.477 |

What is claimed is:

1. A process for the preparation of 1,1,1-trichlorotrifluoroethane in which 1,1-dichloro-2,2,2-trifluoroethane is subjected to chlorination by bringing the 1,1-dichloro-2,2,2-trifluoroethane into contact with chlorine within a reaction vessel characterised in that the process is conducted in the liquid phase in the presence of a chemical free radical initiator under a pressure of from 1 to 20 bar and at a temperature within the range 50 to 120° C., and the product is separated from the reaction mixture by fractional distillation.

2. A process according to claim 1 wherein the 1,1-dichloro-2,2,2-trifluoroethane and chlorine are fed continuously to the reaction vessel.

3. A process according to claim 2 wherein the molar ratio of chlorine/1,1-dichloro-2,2,2-trifluoroethane is within the range 1.0 to 2.0.

4. A process according to claim 3 wherein the molar ratio of chlorine to total chlorinatable hydrogen atoms is within the range 0.5 to 1.0.

5. A process according to any of claim 1 carried out at a pressure within the range 5 to 15 bar.

6. A process according to any of claim 1 carried out at a temperature within the range 80–110° C.

7. A process according to claim 1 in which the chemical free radical initiator is azobisisobutyronitrile.

8. A process according to claim 2 in which the chemical free radical initiator is continuously fed to the reactor vessel.

9. A process according to claim 8 in which the chemical free radical initiator is used in the form of a solution in a non-perhalogenated solvent.

10. A process according to claim 2 carried out at a pressure within the range 7 to 13 bar and a temperature within the range 80 to 120° C. in the presence of azobisisobutyronitrile, wherein the molar ratio of chlorine/1,1-dichloro-2,2,2-trifluoroethane is within the range 1.0 to 2.0.

11. A process according to claim 1 wherein any unreacted 1,1-dichloro-2,2,2-trifluoroethane is collected from the fractionated reaction mixture and recycled into the reaction vessel.

12. A process according to claim 1 wherein any unreacted chlorine is recovered from the fractionated reaction mixture and recycled into the reaction vessel.

* * * * *